United States Patent [19]
Usman et al.

[11] Patent Number: 5,861,288
[45] Date of Patent: Jan. 19, 1999

[54] CATALYTIC DNA

[75] Inventors: Nassim Usman, Boulder, Colo.; Robert J. Cedergren; Pascal Chartrand, both of Montréal, Canada; Stephen C. Harvey, Birmingham, Ala.

[73] Assignees: Ribozyme Pharmaceuticals, Inc., Boulder, Colo.; UAB Research Foundation, Birmingham, Ala.; University of Montreal, Montreal, Canada

[21] Appl. No.: 139,176

[22] Filed: Oct. 18, 1993

[51] Int. Cl.⁶ ............................. C12P 19/34; C12N 15/11
[52] U.S. Cl. ...................... 435/91.53; 435/199; 536/24.5
[58] Field of Search ................. 435/91.1, 172.1, 435/199, 91.53; 536/24.1, 24.5

[56] References Cited

U.S. PATENT DOCUMENTS 5,149,796  9/1992  Rossi et al. ............................ 536/23.2

FOREIGN PATENT DOCUMENTS 9119789  12/1991  WIPO .............................. C12N 9/22
9207065  4/1992  WIPO .
9315187  8/1993  WIPO .

OTHER PUBLICATIONS

Christoffersen et al., *J. Medicinal Chem.*, vol. 38, 1995, pp. 2023–2037.
Stull et al., *Pharmaceutical Res.*, vol. 12, 1995, pp. 465–481.
Gura, *Science*, vol. 270, 1995, pp. 575–577.
Perreault et al., "Mixed Deoxyribo– and Ribo–Oligonucleotides with Catalytic Activity," *Nature* 344:565–567 (1990).
Cech, "The Chemistry of Self–Splicing RNA and RNa Enzymes," *Science* 236:1532–1539 (1987).
Shimayama et al., "Nuclease–resistant chimeric ribozymes containing deoxyribonucleotides and phosphorthioate linkages," *Nucleic Acids Research* 21:2605–2611 (1993).
Jeffries and Symons, "A Catalytic 13–mer Ribozyme," 17 *Nucleic Acids Research* 1371, 1989.
Yang et al., "Mixed DNA/RNA Polymers Are Cleaved by the Hammerhead Ribozyme", 29 *Biochemistry* 11156, 1990.
Perreault et al., "Relationship between 2'–Hydroxyls and Magnesium Binding in the Hammerhead RNA Domain: A Model for Ribozyme Catalysis", 30 *Biochemistry* 4020, 1991.
Yang et al., "Minimum ribonucleotide Requirement for Catalysis by the RNA Hammerhead Domain", 31 *Biochemistry* 5005, 1992.
Usman and Cedergren, "Expoloiting the chemical synthesis of RNA", 17 *Trends in Biochem Sci.* 334, 1992.
Rossi et al., "Ribozymes as Anti–HIV–1 Therapeutic Agents: Principles, Applications, and Problems," 8 *Aids Research and Human Retroviruses* 183, 1992.
Hampel and Tritz, "RNA Catalytic Properties of the Minimum (–)sTRSV Sequence," 28 *Biochemistry* 4929, 1989.
Hampel et al., "'Hairpin' Catalytic RNA Model: Evidence for Helices and Sequence Requirement for Substrate RNA," 18 *Nucleic Acids Research* 299, 1990.
Perrotta and Been, "cleavage of Oligoribonucleotides by a Ribozyme Derived from the Hepatitis δ Virus RNA Sequence," 31 *Biochemistry* 16, 1992.

*Primary Examiner*—James Ketter
*Attorney, Agent, or Firm*—Lyon & Lyon LLP

[57] ABSTRACT

Nucleic acid able to cause specific cleavage of a bond between two ribonucleotides in an RNA-containing molecule. The RNA-containing molecule has the structure:

5'-X$_n$UHZCUGANGAGY$_m$-3' wherein each X and Y is independently any nucleotide base; n and m are independently between 5 and 40; H is U, A or C; Z is a hairpin loop, having between 6 and 60 bases, and each U, C, G and A is a uracil, cytosine, guanosine, or adenosine-containing ribonucleotide, respectively, and N is any ribonucleotide. The nucleic acid has the structure:

3'-X'$_n$M$_0$Y'$_m$-5' wherein each X' and Y' are complementary nucleotide bases to each corresponding X and Y, and M$_0$ is a series of nucleotide bases active to cause the cleavage, and wherein M$_0$ contains no ribonucleotides.

15 Claims, 8 Drawing Sheets

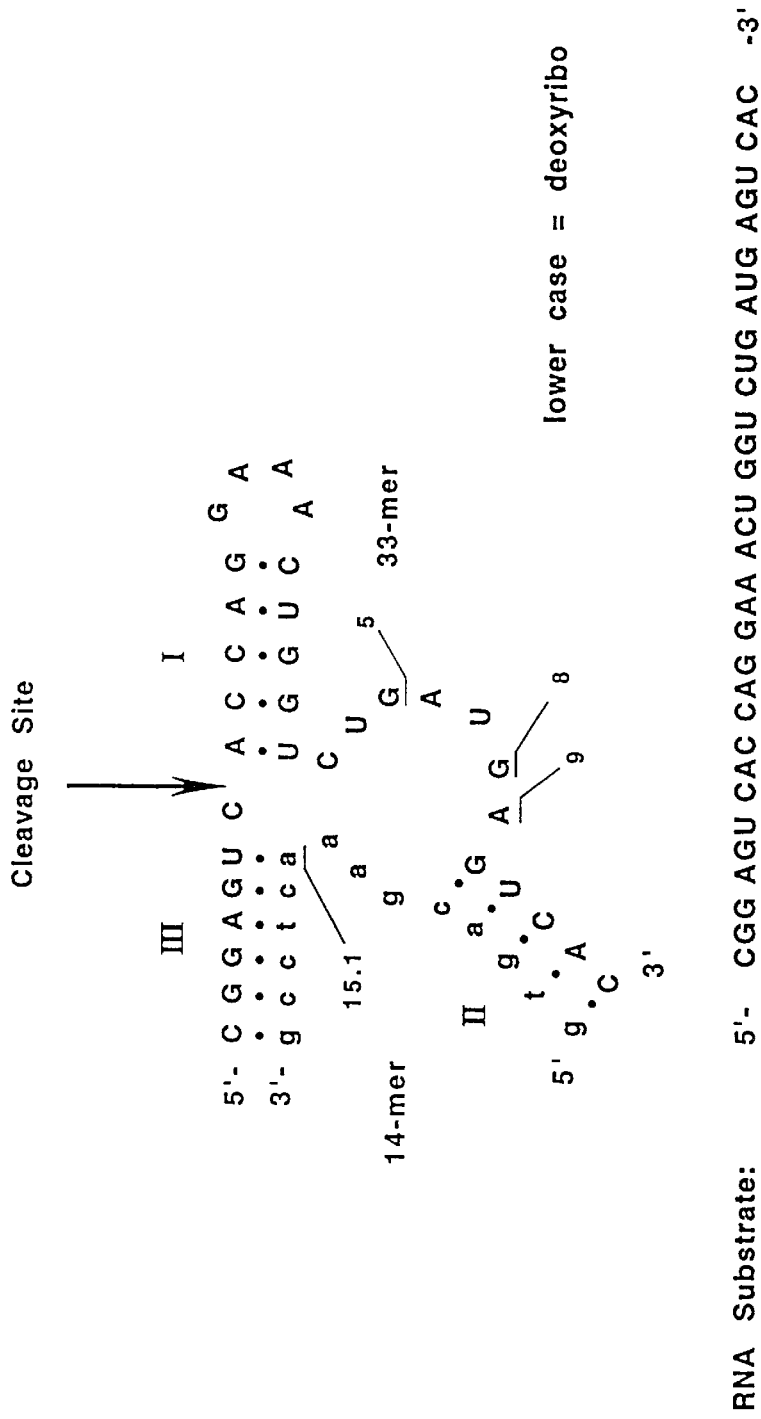

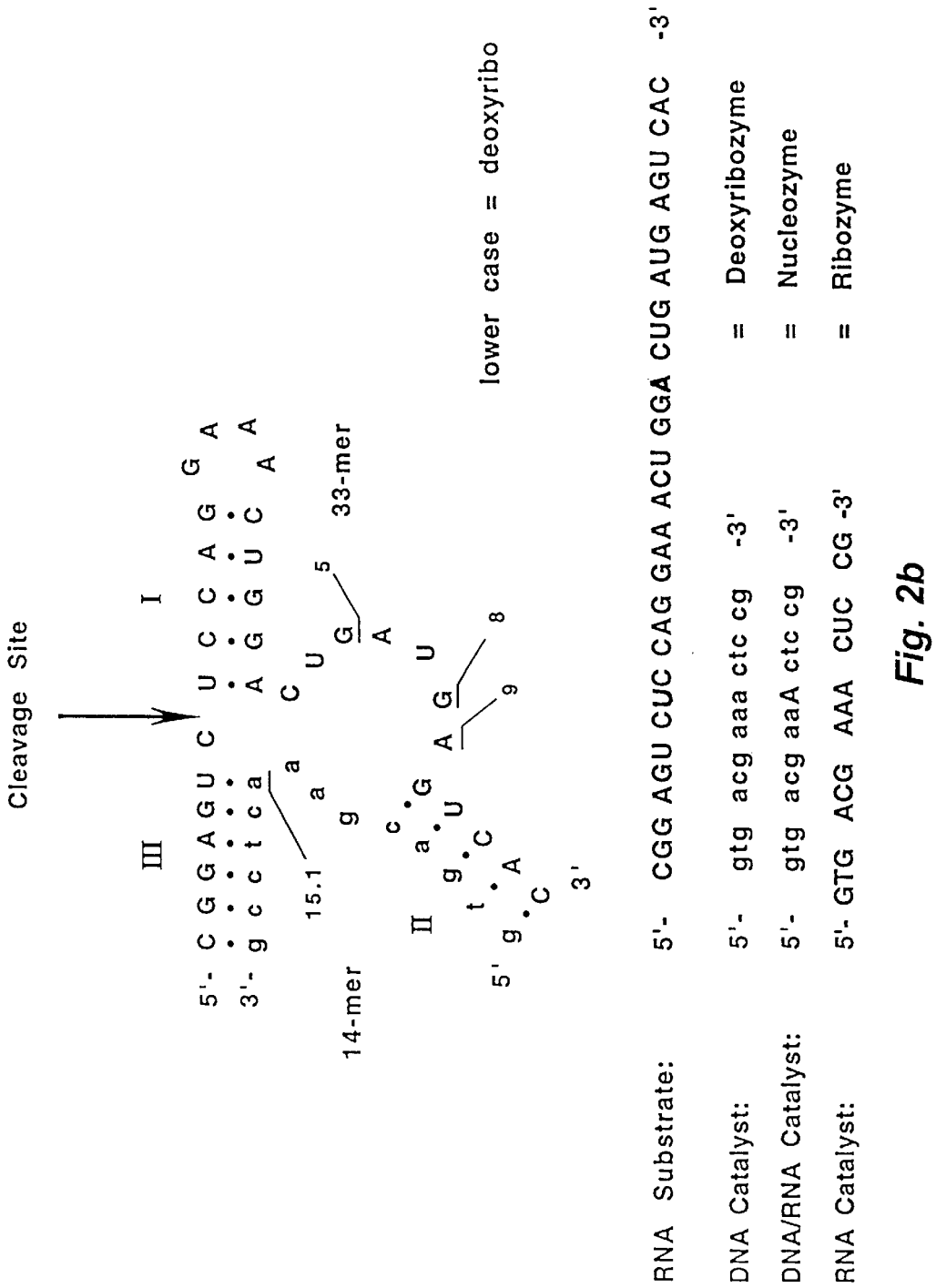

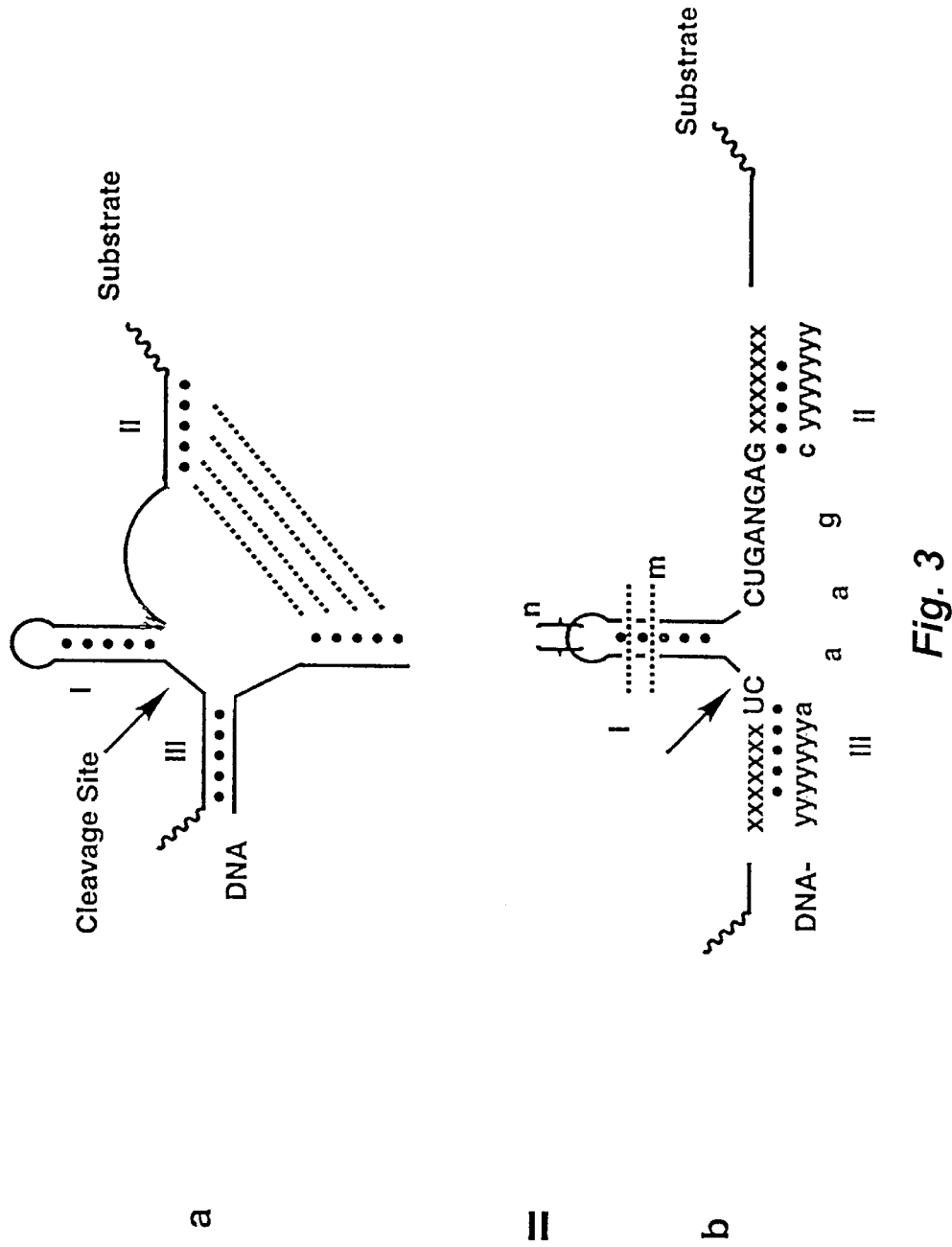

RNA Cleavage by a Deoxyribozyme

CATALYTIC DNA

BACKGROUND OF THE INVENTION

This invention relates to the cleavage of RNA or DNA by a nucleic acid molecule.

The following is a brief history of the discovery and activity of enzymatic RNA molecules or ribozymes. This history is not meant to be complete but is provided only for understanding of the invention that follows. This summary is not an admission that all of the work described below is prior art to the claimed invention.

Prior to the 1970s it was thought that all genes were direct linear representations of the proteins that they encoded. This simplistic view implied that all genes were like ticker tape messages, with each triplet of DNA "letters" representing one protein "word" in the translation. Protein synthesis occurred by first transcribing a gene from DNA into RNA (letter for letter) and then translating the RNA into protein (three letters at a time). In the mid 1970s it was discovered that some genes were not exact, linear representations of the proteins that they encode. These genes were found to contain interruptions in the coding sequence which were removed from, or "spliced out" of, the RNA before it became translated into protein. These interruptions in the coding sequence were given the name of intervening sequences (or introns) and the process of removing them from the RNA was termed splicing. After the discovery of introns, two questions immediately arose: (i) why are introns present in genes in the first place, and (ii) how do they get removed from the RNA prior to protein synthesis? The first question is still being debated, with no clear answer yet available. The second question, how introns get removed from the RNA, is much better understood after a decade and a half of intensive research on this question. At least three different mechanisms have been discovered for removing introns from RNA. Two of these splicing mechanisms involve the binding of multiple protein factors which then act to correctly cut and join the RNA. A third mechanism involves cutting and joining of the RNA by the intron itself, in what was the first discovery of catalytic RNA molecules.

Cech and colleagues were trying to understand how RNA splicing was accomplished in a single-celled pond organism called *Tetrahymena thermophila*. They had chosen *Tetrahymena thermophila* as a matter of convenience, since each individual cell contains over 10,000 copies of one intron-containing gene (the gene for ribosomal RNA). They reasoned that such a large number of intron-containing RNA molecules would require a large amount of (protein) splicing factors to remove the introns quickly. Their goal was to purify these hypothesized splicing factors and to demonstrate that the purified factors could splice the intron-containing RNA in vitro. Cech rapidly succeeded in getting RNA splicing to work in vitro, but something unexpected was occurring. As expected, splicing occurred when the intron-containing RNA was mixed with protein-containing extracts from Tetrahymena, but splicing also occurred when the protein extracts were left out. Cech proved that the intervening sequence RNA was acting as its own splicing factor to snip itself out of the surrounding RNA. They published this startling discovery in 1982. Continuing studies in the early 1980's served to elucidate the complicated structure of the Tetrahymena intron and to decipher the mechanism by which self-splicing occurs. Many research groups helped to demonstrate that the specific folding of the Tetrahymena intron is critical for bringing together the parts of the RNA that will be cut and spliced. Even after splicing is complete, the released intron maintains its catalytic structure. As a consequence, the released intron is capable of carrying out additional cleavage and splicing reactions on itself (to form intron circles). By 1986, Cech was able to show that a shortened form of the Tetrahymena intron could carry out a variety of cutting and joining reactions on other pieces of RNA. The demonstration proved that the Tetrahymena intron can act as a true enzyme: (i) each intron molecule was able to cut many substrate molecules while the intron molecule remained unchanged, and (ii) reactions were specific for RNA molecules that contained a unique sequence (CUCU) which allowed the intron to recognize and bind the RNA. Zaug and Cech coined the term "ribozyme" to describe any ribonucleic acid molecule that has enzyme-like properties. Also in 1986, Cech showed that the RNA substrate sequence recognized by the Tetrahymena ribozyme could be changed by altering a sequence within the ribozyme itself. This property has led to the development of a number of site-specific ribozymes that have been individually designed to cleave at other RNA sequences. The Tetrahymena intron is the most well-studied of what is now recognized as a large class of introns, Group I introns. The overall folded structure, including several sequence elements, is conserved among the Group I introns, as is the general mechanism of splicing. Like the Tetrahymena intron, some members of this class are catalytic, i.e., the intron itself is capable of the self-splicing reaction. Other Group I introns require additional (protein) factors, presumably to help the intron fold into and/or maintain its active structure. While the Tetrahymena intron is relatively large, (413 nucleotides) a shortened form of at least one other catalytic intron (SunY intron of phage T4, 180 nucleotides) may prove advantageous not only because of its smaller size but because it undergoes self-splicing at an even faster rate than the Tetrahymena intron.

Ribonuclease P (RNaseP) is an enzyme comprised of both RNA and protein components which are responsible for converting precursor tRNA molecules into their final form by trimming extra RNA off one of their ends. RNaseP activity has been found in all organisms tested, but the bacterial enzymes have been the most studied. The function of RNaseP has been studied since the mid-1970s by many labs. In the late 1970s, Sidney Altman and his colleagues showed that the RNA component of RNaseP is essential for its processing activity; however, they also showed that the protein component was also required for processing under their experimental conditions. After Cech's discovery of self-splicing by the Tetrahymena intron, the requirement for both protein and RNA components in RNaseP was reexamined. In 1983, Altman and Pace showed that the RNA was the enzymatic component of the RNaseP complex. This demonstrated that an RNA molecule was capable of acting as a true enzyme, processing numerous tRNA molecules without itself undergoing any change. The folded structure of RNaseP RNA has been determined, and while the sequence is not strictly conserved between RNAs from different organisms, this higher order structure is. It is thought that the protein component of the RNaseP complex may serve to stabilize the folded RNA in vivo. At least one RNA position important both to substrate recognition and to determination of the cleavage site has been identified, however little else is known about the active site. Because tRNA sequence recognition is minimal, it is clear that some aspect(s) of the tRNA structure must also be involved in substrate recognition and cleavage activity. The size of RNaseP RNA (>350 nucleotides), and the complexity of the substrate recognition, may limit the potential for the use of an RNaseP-like RNA in therapeutics. However, the size of RNaseP is being trimmed down (a molecule of only 290 nucleotides functions reasonably well). In addition, substrate recognition has been simplified by the recent discovery that RNaseP RNA can cleave small RNAs lacking the natural tRNA secondary structure if an additional RNA (containing a "guide" sequence and a sequence element naturally present at the end of all tRNAs) is present as well.

Symons and colleagues identified two examples of a self-cleaving RNA that differed from other forms of catalytic RNA already reported. Symons was studying the propagation of the avocado sunblotch viroid (ASV), an RNA virus that infects avocado plants. Symons demonstrated that as little as 55 nucleotides of the ASV RNA was capable of folding in such a way as to cut itself into two pieces. It is thought that in vivo self-cleavage of these RNAs is responsible for cutting the RNA into single genome-length pieces during viral propagation. Symons discovered that variations on the minimal catalytic sequence from ASV could be found in a number of other plant pathogenic RNAs as well. Comparison of these sequences revealed a common structural design consisting of three stems and loops connected by central loop containing many conserved (invariant from one RNA to the next) nucleotides. The predicted secondary structure for this catalytic RNA reminded the researchers of the head of a hammer consisting of three double helical domains, stems I, II and III and a catalytic core (FIG. 1*a*); thus it was named as such. Uhlenbeck was successful in separating the catalytic region of the ribozyme from that of the substrate. Thus, it became possible to assemble a hammerhead ribozyme from 2 (or 3) small synthetic RNAs. A 19-nucleotide catalytic region and a 24-nucleotide substrate, representing division of the hammerhead domain along the axes of stems I and II (FIG. 1*b*) were sufficient to support specific cleavage. The catalytic domain of numerous hammerhead ribozymes have now been studied by both the Uhlenbeck and Symons groups with regard to defining the nucleotides required for specific assembly and catalytic activity and determining the rates of cleavage under various conditions.

Haseloff and Gerlach showed it was possible to divide the domains of the hammerhead ribozyme in a different manner, division of the hammerhead domain along the axes of stems I and III (see, FIG. 1*c*). By doing so, they placed most of the required sequences in the strand that didn't get cut (the ribozyme) and only required a UH where H=C, A, U in the strand that did get cut (the substrate). This resulted in a catalytic ribozyme that could cleave a UH-containing RNA sequence embedded within a longer "substrate recognition" sequence. The specific cleavage of a long mRNA, in a predictable manner using several such hammerhead ribozymes, was reported in 1988. A further development was the division of the catalytic hammerhead domain along the axes of stems III and II (FIG. 1*d*, Jeffries and Symons, *Nucl. Acids. Res.* 1989, 17:1371.)

Deoxyribonucleotide substitutions in the fragment corresponding to construct 1*c* have been described by Yang et al., *Biochemistry* 1990, 29:11156; Perreault et al., *Biochemistry* 1991, 30:4020; Yang et al., *Biochemistry* 1992, 31:5005; Usman and Cedergren, *Trends in Biochem. Sci.* 1992, 17:334; Usman et al, International Publication No. WO 92/07065; Eckstein et al., International Publication No. WO 93/15187; and Rossi et al., U.S. Pat. No. 5,149,796. Jeffries and Symons, supra, indicated that DNA used in construct 1*d* does not catalyze the cleavage of RNA.

One plant pathogen RNA (from the negative strand of the tobacco ringspot virus) undergoes self-cleavage but cannot be folded into the consensus hammerhead structure described above. Bruening and colleagues have independently identified a 50-nucleotide catalytic domain for this RNA. In 1990, Hampel and Tritz succeeded in dividing the catalytic domain into two parts that could act as substrate and ribozyme in a multiple-turnover, cutting reaction. As with the hammerhead ribozyme, the hairpin catalytic portion contains most of the sequences required for catalytic activity while only a short sequence (GUC in this case) is required in the target. Hampel and Tritz described the folded structure of this RNA as consisting of a single hairpin and coined the term "hairpin" ribozyme (Bruening and colleagues use the term "paper clip" for this ribozyme motif). Continuing experiments indicate an increasing number of similarities between the hairpin and hammerhead ribozymes in respect to both binding of target RNA and mechanism of cleavage. At the same time, the minimal size of the hairpin ribozyme is still 50–60% larger than the minimal hammerhead ribozyme.

Hepatitis Delta Virus (HDV) is a virus whose genome consists of single-stranded RNA. A small region (about 80 nucleotides) in both the genomic RNA, and in the complementary anti-genomic RNA, is sufficient to support self-cleavage. As the most recently discovered ribozyme, HDV's ability to self-cleave has only been studied for a few years, but is interesting because of its connection to a human disease. In 1991, Been and Perrotta proposed a secondary structure for the HDV RNAs that is conserved between the genomic and anti-genomic RNAs and is necessary for catalytic activity. Separation of the HDV RNA into "ribozyme" and "substrate" portions has recently been achieved by Been. Been has also succeeded in reducing the size of the HDV ribozyme to about 60 nucleotides.

The table below lists some of the characteristics of the ribozymes discussed above:

TABLE 1

Characteristics of Ribozymes

Group I Introns

Size: ~300 to >1000 nucleotides.
Requires a U in the target sequence immediately 5' of the cleavage site.
Binds 4–6 nucleotides at the 5'-side of the cleavage site.
Over 75 known members of this class. Found in *Tetrahymena thermophila* rRNA, fungal mitochondria, chloroplasts, phage T4, blue-green algae, and others.

RNaseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Size: ~30 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)

Hairpin Ribozyme

Size: ~50 nucleotides.
Requires the target sequence GUC immediately 3' of the cleavage site.
Binds 4 nucleotides at the 5'-side of the cleavage site and a

TABLE 1-continued

Characteristics of Ribozymes variable number to the 3'-side of the cleavage site.
Only 1 known member of this class. Found in one plant pathogen
(satellite RNA of the tobacco ringspot virus) which uses RNA as
the infectious agent (FIG. 5).

Hepatitis Delta Virus (HDV) Ribozyme

Size: ~60 nucleotides (at present).
Cleavage of target RNAs recently demonstrated.
Sequence requirements not fully determined.
Binding sites and structural requirements not fully determined,
although no sequences 5' of the cleavage site are required.
Only 1 known member of this class. Found in human HDV
(FIG. 6).

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

SUMMARY OF THE INVENTION

This invention concerns the cleavage of RNA by catalytic DNA or non-RNA-containing DNA-chimeras referred to as Deoxyribozymes, specifically cleavage by small deoxyribozymes, such as those which (together with their target RNA) form the motif referred to as hammerhead, hairpin, or hepatitis D virus. This activity in such deoxyribozymes is achieved by chemical synthesis of a deoxyribozyme.

Specifically, we describe the use of a construct similar to FIG. 1d as a general scheme for nucleic acid able to cleave RNA. More specific examples are shown in FIGS. 2a and 2b, and a general scheme of the substrate repertoire available for such nucleic acid is shown in FIG. 3.

A specific example of the DNA catalyzed cleavage of a 33-mer RNA strand (S) to a 7-mer product (P) is shown in FIG. 4. The ratio of catalytic activity of the DNA catalyzed cleavage (lane 6) vs the RNA catalyzed (lane 4) and DNA-RNA chimera (lane 2) is about 1/10/8. Lanes 1, 3 and 5 show the same reactions following incubation of the enzymes with 10 mM NaOH at 80° C. As expected, the enzymatic activities of the ribozyme (lane 3) and the chimera (lane 1) are abolished, whereas the catalytic activity of the DNA only nucleic acid (lane 5) is maintained. We further show that other non-RNA-containing fragments also catalyze the RNA cleavage reaction.

As the term is used in this application, catalytic DNA enzymes, or Deoxyribozymes, are DNA, or non-RNA-containing DNA chimera molecules having an enzymatic activity which is able to cleave (preferably, repeatedly cleave) separate RNA molecules in a nucleotide base sequence specific manner.

Deoxyribozymes act by first binding to a target RNA. Such binding occurs through the DNA binding portion of a deoxyribozyme which is held in close proximity to the RNA (provided by the substrate) which acts to cleave the target RNA. Thus, the deoxyribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a deoxyribozyme has bound and cleaved its RNA target it is released from that RNA to search for another target and can repeatedly bind and cleave new targets.

By the phrase "enzymatic DNA molecule" is meant a DNA molecule which has complementarity in a substrate binding region to a specified gene target, and also is able to cause specific cleavage of RNA in that target. That is, the enzymatic DNA molecule is able to intermolecularly cleave RNA and thereby inactivate a target RNA molecule. This complementarity functions to allow sufficient hybridization of the DNA molecule to the target RNA to allow the cleavage to occur. One hundred percent complementarity is preferred, but complementarity as low as 50–75% may also be useful in this invention.

In preferred embodiments of this invention, the enzymatic DNA molecule, in conjunction with its target RNA, is formed in a hammerhead motif, but may also be formed in the motif of a hairpin or hepatitis delta virus. Examples of such hammerhead motifs are described by Rossi et al., *Aids Research and Human Retroviruses* 1992, 8:183; of hairpin motifs by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, *Biochemistry* 1989, 28:4929, and Hampel et al, *Nucleic Acids Research* 1990, 18:299; and an example of the hepatitis delta virus motif is described by Perrotta and Been, *Biochemistry* 1992, 31:16. These specific motifs are not limiting in the invention and those skilled in the art will recognize that all that is important in a DNA molecule of this invention is that it has a specific substrate binding site which is complementary to one or more of the target gene RNA regions, and that it have nucleotide sequences within that substrate binding site which impart an RNA cleaving activity to the molecule.

The invention provides a method for producing a class of enzymatic cleaving agents that exhibit a high degree of specificity for the RNA of a desired target. The deoxyribozyme molecule is preferably targeted to a highly conserved sequence region of a target such that specific treatment of a disease or condition can be provided with a single deoxyribozyme. Such enzymatic DNA molecules can be delivered exogenously to specific cells as required. The preferred DNA molecule is small in size (less than 30 nucleotides, preferably between 13–20 nucleotides in length) so that the molecule allows the cost of treatment to be reduced compared to other ribozyme motifs.

Synthesis of ribozymes greater than 100 nucleotides in length is difficult using automated methods, and the therapeutic cost of such molecules is prohibitive. In this invention, small deoxyribozyme motifs (e.g., of the hammerhead structure) are used for exogenous delivery. The simple structure of these molecules increases the ability of the deoxyribozyme to invade targeted regions of the mRNA structure. Unlike the situation when the hammerhead structure is included within longer transcripts, there are no non-deoxyribozyme flanking sequences to interfere with correct folding of the deoxyribozyme structure or with complementary regions.

Thus, in a first aspect, the invention features nucleic acid able to cause specific cleavage of a bond between two ribonucleotides in an RNA molecule. The RNA molecule has the structure:

5'-XnUHZCUGANGAGYm-3' (SEQ. ID. NO. 1)

wherein, each X and Y is independently any nucleotide base; n and m are independently between 5 and 40; H is U, A or C; Z is a hairpin loop, having between 1 and 60 bases, preferably between 6 and 30 bases, and each U, C, G and A is a uracil, cytosine, guanosine, or adenosine-containing ribonucleotide, respectively, and N is any ribonucleotide. The nucleic acid has the structure:

3'-X'nM$_0$Y'm-5' wherein, each X' and Y' are complementary nucleotide bases to each corresponding X and Y, and M$_0$ is a series of nucleotide bases (0 in number) active to cause the cleavage. M$_0$ contains no ribonucleotides.

In preferred embodiments, M$_0$ is 3'-aaagc-5', wherein a, g and c are adenosine, guanosine and cytosine-containing deoxyribonucleotides, respectively; M$_0$ has at least one non-deoxynucleotide base; M$_0$ has all deoxyribonucleotide bases; X', M$_0$ and Y' have all deoxyribonucleotide bases; and M$_0$ has between 5 and 10 bases. Most preferably, the RNA-containing molecule has the structure:

5'-XnUCACCAGGAAACUGGUCUGANGAGYm-3' (SEQ. ID. NO. 2)

or

5=-XnUCUCCAGGAAACUGGACUGANGAGYm-3' (SEQ. ID. NO. 3)

and the nucleic acid has the structure:

3'-gcctcaaagcagtg-5' (SEQ. ID. NO. 4)

wherein, g, c, t and a are guanosine, cytosine, thymine and adenosine-containing deoxyribonucleotides.

In a second aspect, the invention features a method for causing specific cleavage of a bond between two nucleotides in an RNA-containing molecule having the structure shown above in Seq. ID. No. 1, including the steps of contacting the RNA-containing molecules with nucleic acid having the structure:

3'-X'nM$_0$Y'm-5' wherein, each X' and Y' are complementary nucleotide bases to each corresponding X and Y, and M$_0$ is a series of nucleotide bases (0 in number) active to cause the cleavage, under bond-cleaving conditions.

By "hairpin loop" is simply meant a structure which does not interfere with cleavage by the deoxyribozyme which generally contains about 4 to 7 base paired nucleotides with a small loop of between 4 and 8 nucleotides. Specifically, referring to FIG. 3, m in that figure is between 4 and 8, and n in that figure is between 4 and 8.

Applicant is the first to discover that completely non-ribonucleotide-containing molecules can be used to cause specific cleavage of RNA-containing molecules in a catalytic or enzymatic fashion. This contrasts with the work of Jeffries and Symons who were unable to achieve this result. While an example in the hammerhead motif is provided below, those in the art will recognize that equivalent hairpin and hepatitis delta virus constructs can be readily formed. Optimization of a desirable deoxyribonucleotide deoxyribozyme can be achieved using standard methodology, and in vitro selection protocols can be readily devised to select optimum DNA molecules having such cleavage causing activity.

Other features and advantages of the invention will be apparent from the following description of the preferred embodiments thereof, and from the claims.

DESCRIPTION OF THE PREFERRED EMBODIMENTS

Figure 1:
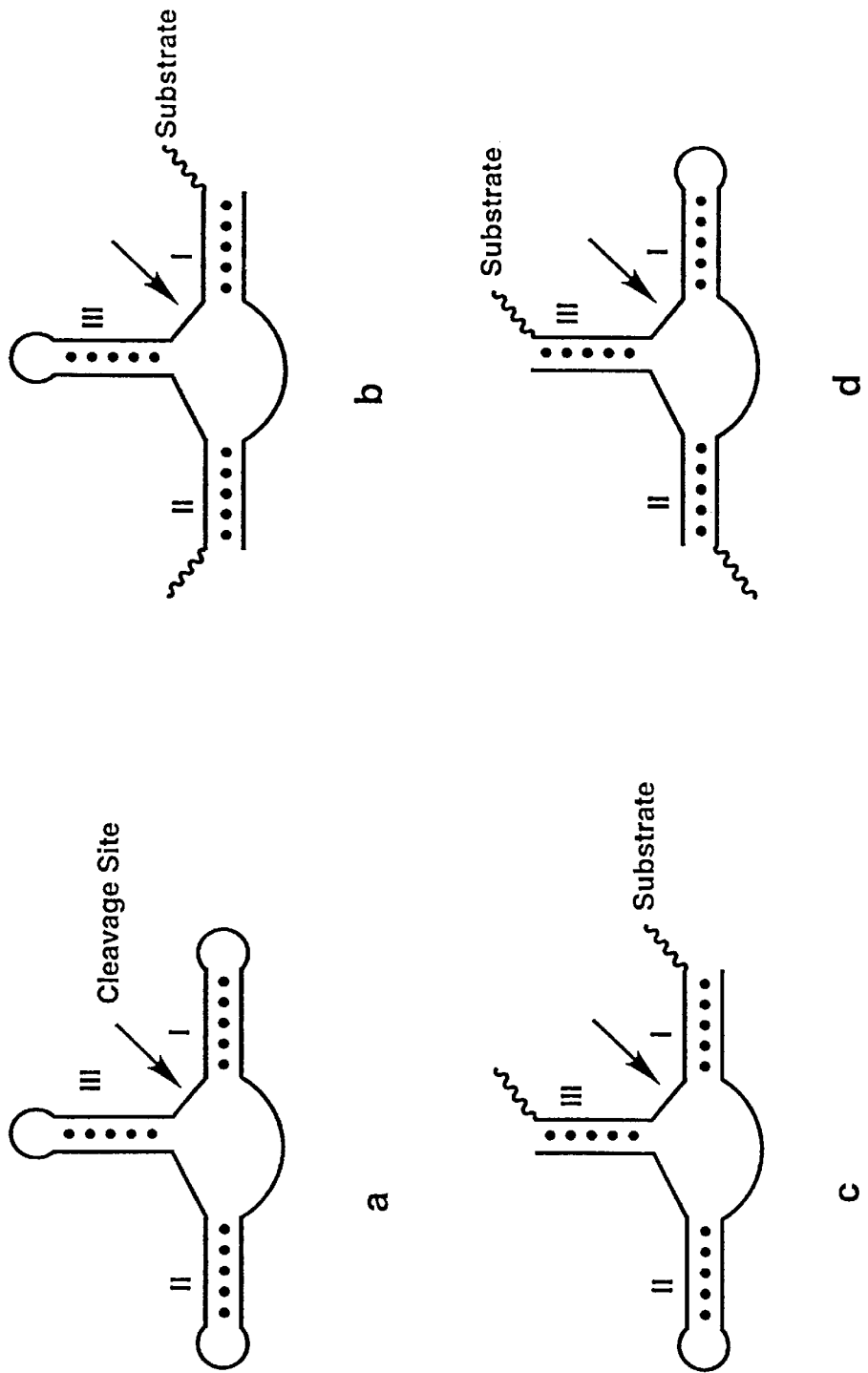

The drawings will first briefly be described.
Drawings:

FIG. 1a is a diagrammatic representation of the hammerhead ribozyme domain known in the art; FIG. 1b is a diagrammatic representation of the hammerhead ribozyme as divided by Uhlenbeck into a substrate and enzyme portion; FIG. 1c is a similar diagram showing the hammerhead divided by Haseloff and Gerlach into two portions; and FIG. 1d is a similar diagram showing the hammerhead divided by Jeffries and Symons into two portions.

FIGS. 2a and 2b are representations of specific examples of the cleavage of RNA by a catalytic DNA strand in the hammerhead domain. In FIG. 2a: RNA Substrate (SEQ. ID. NO. 8), DNA Catalyst (SEQ. ID. NO. 7), DNA/RNA Catalyst (SEQ. ID. NO. 7), and Catalyst (SEQ. ID. NO. 9). In FIG. 2b: RNA Substrate (SEQ. ID. NO. 10), DNA Catalyst (SEQ. ID. NO. 11), DNA/RNA Catalyst (SEQ. ID. NO. 7), RNA Catalyst (SEQ. ID. NO. 9).

FIG. 3 is a representation of the general structure of any substrate RNA molecule able to participate in the DNA mediated catalysis of RNA cleavage. Substrate (SEQ. ID. NO. 15), Catalytic DNA (SEQ. ID. NO. 16).

Figure 4:
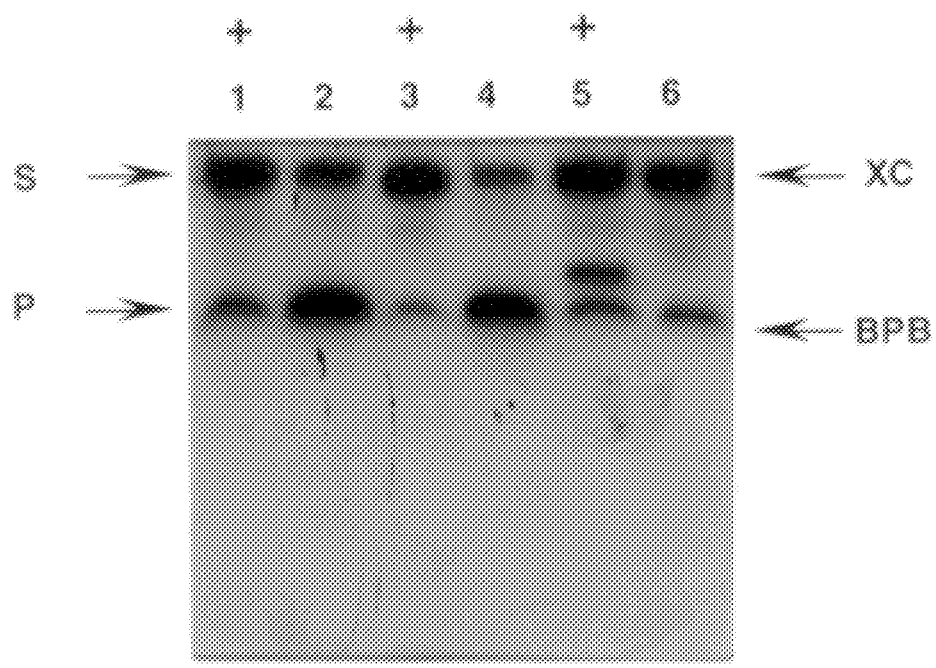

FIG. 4 is an autoradiogram showing the cleavage of an RNA substrate by a catalytic DNA strand of the structure shown in FIG. 2.

Specifically: Autoradiogram of a 20% polyacrylamide/7M urea gel of $^{32}$P 5'-end labeled RNA substrate (S) cleavage reactions (P=product). Cleavage by deoxyribozyme (D), chimeric nucleozyme (N) and standard ribozyme (R) molecules were at 30° C. in 10 mM Mg$^{2+}$ with [E]/[S]=1 unless otherwise noted. A + indicates the addition of NaOH. Lanes: 1) S+N+NaOH, 2) S+N, 3) S+R+NaOH, 4) S+R, 5)S+D+NaOH, 6) S+D. The positions of xylene cyanol FF dye (XC) and bromophenol blue dye (BP) are indicated.

Figure 5:
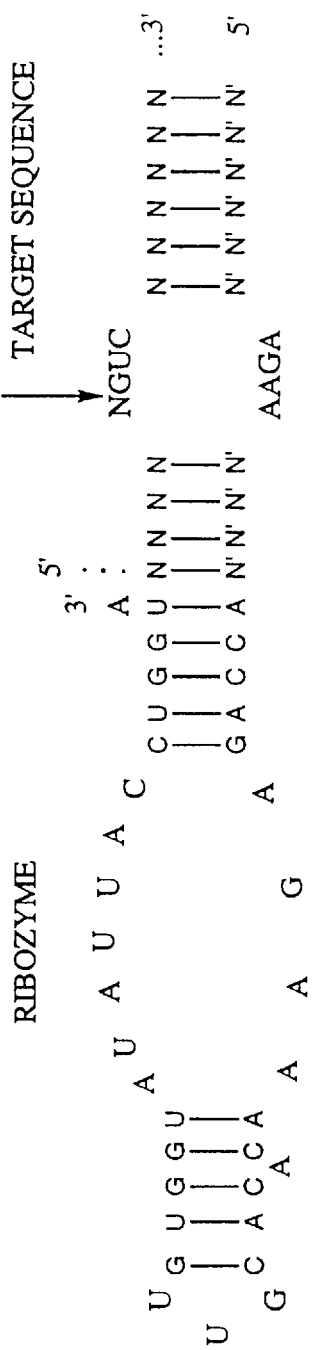

FIG. 5 is a representation of general structure of the hairpin ribozyme domain known in the art. Target Sequence (SEQ. ID. NO. 12), Ribozyme (SEQ. ID. NO. 13).

Figure 6:
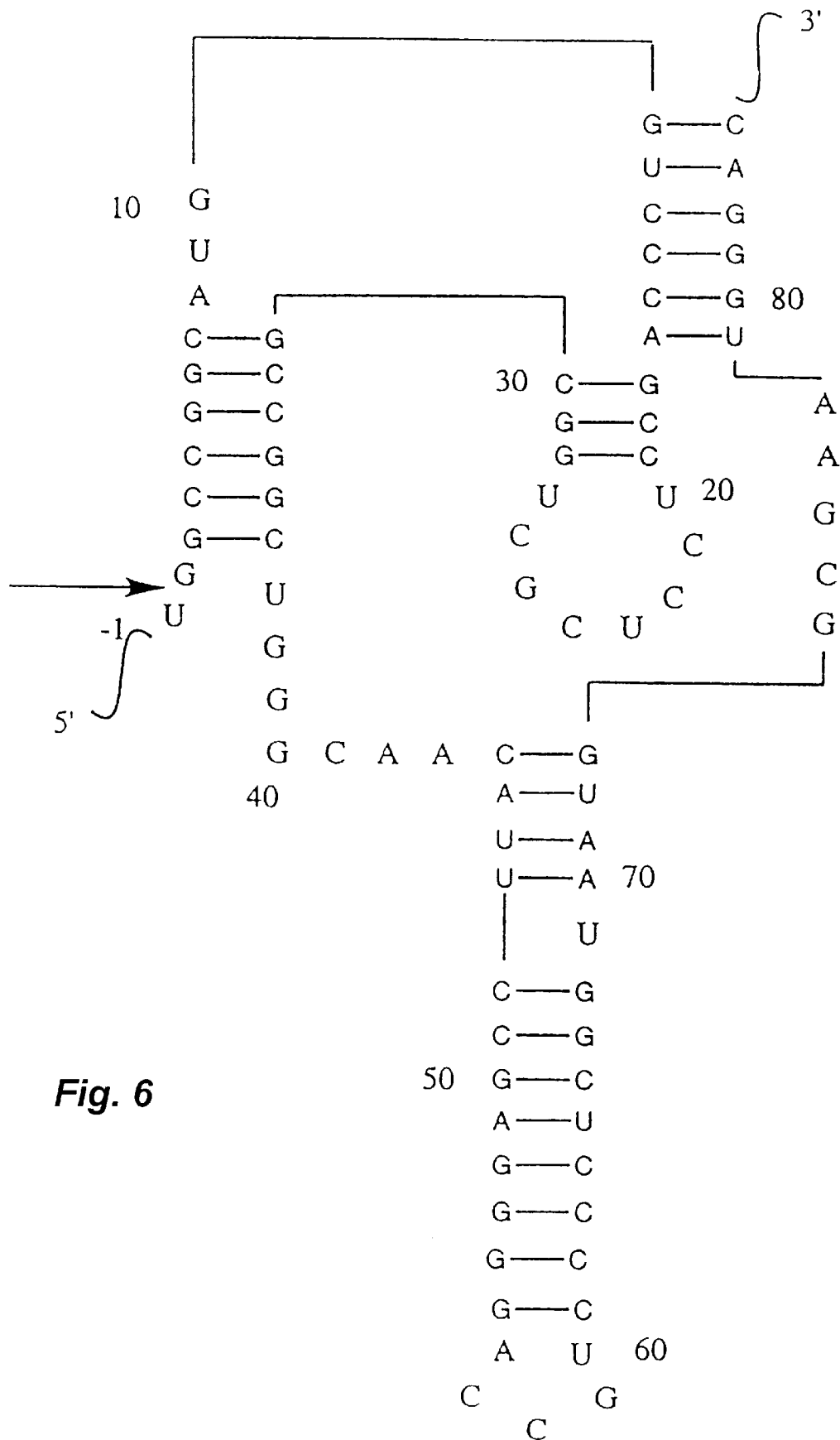

FIG. 6 is a representation of general structure of the hepatitis delta virus ribozyme domain known in the art (SEQ. ID. NO. 14).

Figure 7:
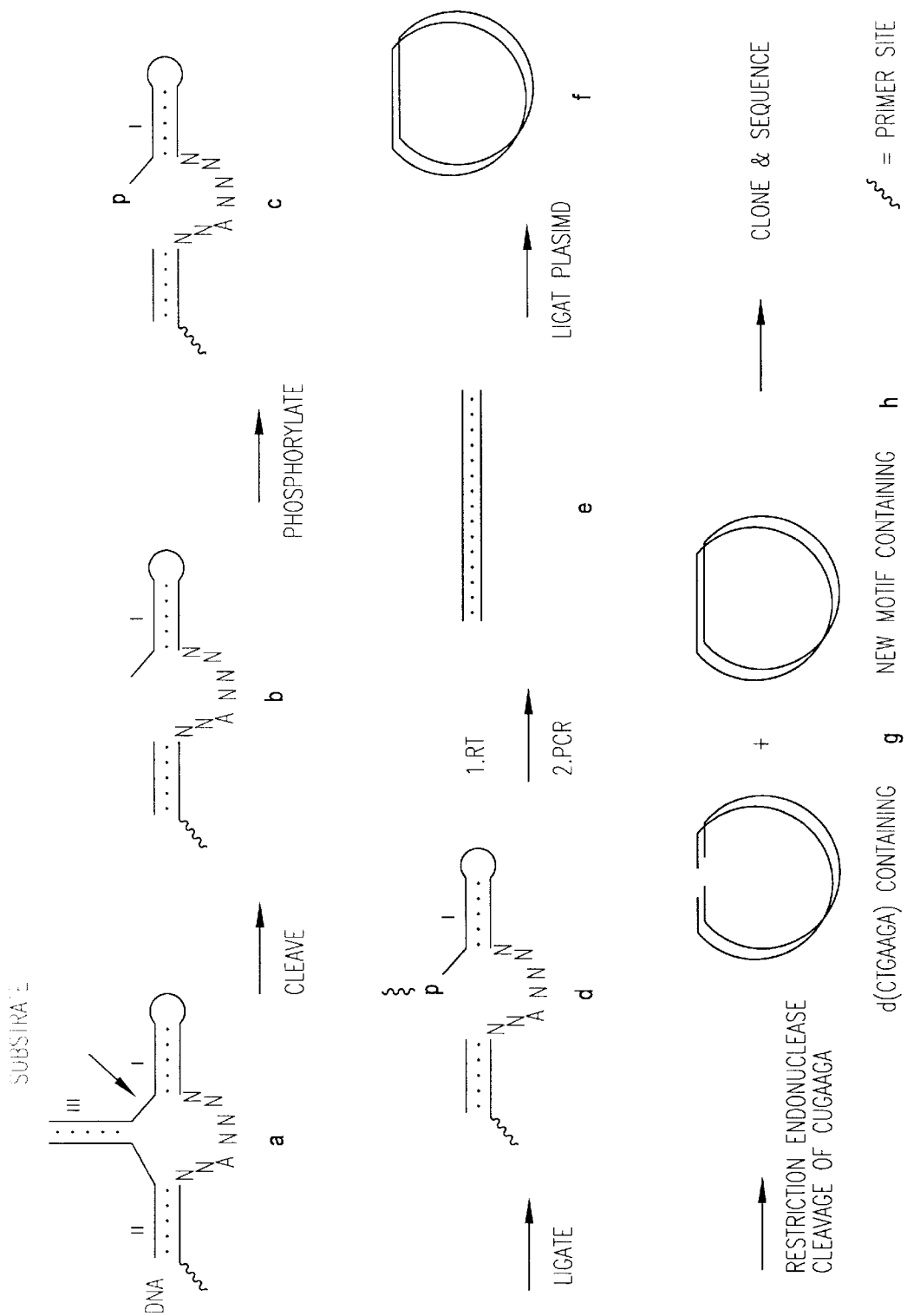

FIG. 7 is a representation of a selection protocol for other catalytic substrate domains for deoxyribozymes.
RNA Cleaving Deoxyribozymes:

RNA cleaving deoxyribozymes useful in this invention are generally described above. These deoxyribozymes are generally formed from deoxyribonucleotides, but such deoxyribonucleotides can be modified from those occurring in nature to have different chemical substituents in the 2' position (see, Usman, supra, and Eckstein, supra), as well as modified bases well known in the art.

EXAMPLES

The following are non-limiting examples showing the synthesis of non-nucleotide mimetic containing catalytic nucleic acids using non-nucleotide phosphoramidites.

Example 1

Cleavage of 5'-CGG AGU CAC CAG GAA ACU GGU GUG AUG AGU CAC (SEQ ID NO. 5)-3' by 5'-d(gtg acg aaa ctc cg)-3' (SEQ ID NO. 6)

The substrate molecule (S) shown in FIG. 2a was 5'-end labeled with $^{32}P$ and purified by PAGE. The cleavage of S was affected by a deoxyribozyme (D), 5'-d(gtg acg aaa ctc cg)-3' (SEQ ID NO. 6) a nucleozyme (N), 5'-d(gtg acg aar(A) ctc cg)-3' (SEQ ID NO. 7), and a ribozyme (R), 5'-GTG ACG AAA CTC CG-3' (SEQ ID NO. 6) at 30° C. in 10 mM $Mg^{2+}$ with [E]/[S]=1 (lanes 6, 2 and 4, respectively, in FIG. 4). As a control for the catalytic cleavage by the deoxyribozyme, all three enzymes were pre-treated with 10 mM NaOH at 80° C. (lanes 5, 1 and 3, respectively, in FIG. 4). This pre-treatment cleaves any RNA-containing enzyme and thereby abolishes its enzymatic activity. This was seen in the case of the nucleozyme (N) reaction, cleavage in lane 2 was abolished in lane 1, and in the case of the ribozyme (R) reaction, cleavage in lane 4 was abolished in lane 3. In the case of the deoxyribozyme (D) reaction, cleavage in lane 6 was not abolished in lane 5. The ratio of catalytic activity of the DNA catalyzed cleavage (lane 6) vs the RNA catalyzed (lane 4) and DNA-RNA chimera (nucleozyme, lane 2) was about 1/10/8.

Example 2

Site Searches

The general utility of using the method of RNA cleavage is illustrated by a search of the HSV genome. The ~156,000 bp HSV genome was searched using GeneWorks_V2.0 Software (IntelliGenetics, Mountain View, Calif.). The search parameter used was to find CUGANGAG. A total of eight sites were found, two of which were in the coding region. The site # from the 5'-end, gene product, coding or non-coding status and whether the site is in the + or − strand are listed below.

| | | | |
|---|---|---|---|
| 10068 | UL2 | Non-Coding | − |
| 56919 | UL28 | Non-coding | + |
| 65123 | UL30 | Non-Coding | − |
| 90571 | UL40 | Non-Coding | − |
| 93596 | UL42 | Coding | + |
| 93650 | UL42 | Coding | + |
| 101268 | UL47 | Non-Coding | + |
| 143338 | US9 | Non-Coding | − |

These sites are potentially useful targets for deoxyribozymes of the present invention. Other such searches can be performed using narrower search terms for the generic structure shown in FIG. 3.

Example 3

In vitro Selection of New Motifs

To expand the repertoire of substrate motifs beyond the CUGANGAG example an in vitro selection strategy may be used to find other sites/motifs. This strategy is illustrated in FIG. 7. In this strategy a synthetic substrate population a containing randomized bases at the positions denoted as "N", is subjected to cleavage with a catalytic DNA molecule (this population may be generated either by chemical synthesis of RNA containing randomized ribonucleotides "N" or by the chemical synthesis of DNA containing randomized deoxyribonucleotides "N" followed by transcription with T7 RNA polymerase). The resulting cleavage product population b is phosphorylated (p) to yield population c. This then allows for the ligation of a PCR primer site to the cleavage product population to yield a tagged population d. Conversion of the tagged RNA population d to DNA via reverse transcriptase followed by PCR of the resulting tagged DNA population gives a double-stranded DNA population e containing the sequences capable of supporting DNA catalyzed RNA cleavage. Population e is then ligated into a plasmid to give a closed circular double-stranded plasmid population f. Subjecting plasmid population f to cleavage by the restriction endonuclease Eco57 i, cleavage sequence 5'-d (CTGAAGA)-3', yields two populations of molecules g and h. Population g contains all wild-type sequences while population h contains new motif sequences. The new motif sequences can then be identified by cloning and sequencing population h. This method can be varied by changing the number of "N" nucleotides in population a.

Other embodiments are within the following claims.

We claim:

1. Nucleic acid able to cause specific cleavage of a bond between two ribonucleotides in an RNA-containing molecule having the structure: 5'-XnUHZCUGANGAGYm-3' (see SEQ. ID NO. 1) wherein each X and Y is independently any nucleotide base; n and m are independently between 5 and 40; H is C, A or U; Z is a hairpin loop, comprising between 6 and 60 bases, and each U, C, G and A is a uracil, cytosine, guanosine, or adenosine-containing ribonucleotide, respectively, and N is any ribonucleotide;

wherein said nucleic acid has the structure: 3'-X'nM$_0$Y'm-5' wherein each X' and Y' are complementary nucleotide bases to each corresponding X and Y, and M$_0$ is a series of nucleotide bases active to cause said cleavage; wherein M$_0$ contains no ribonucleotides, and wherein M$_0$ is a series of nucleotide bases active to cause said cleavage and comprises the sequence 3'-aaag-5'.

2. The nucleic acid of claim 1, wherein M$_0$ is 3'-aaagc-5', wherein a, g and c are adenosine, guanosine and cytosine-containing deoxyribonucleotides, respectively.

3. The nucleic acid of claim 1, wherein said RNA-containing molecule has the structure chosen from:

5'-XnUCACCAGGAAACUGGUCUGANGAGYm-3' (see SEQ. ID NO. 2)

and

5'-XnUCUCCAGGAAACUGGACUGANGAGYm-3' (see SEQ. ID NO. 3).

4. The nucleic acid of claim 3, wherein said nucleic acid has the structure:

3'-gcctcaaagcagtg-5' (see SEQ. ID NO. 4)

wherein, g, c, t and a are guanosine, cytosine, thymine and adenosine-containing deoxyribonucleotides.

5. The nucleic acid of claim 1, wherein M$_0$ comprises at least one non-deoxynucleotide base.

6. The nucleic acid of claim 1, wherein M$_0$ comprises all deoxyribonucleotide bases.

7. The nucleic acid of claim 1, wherein X', M$_0$ and Y' comprise all deoxyribonucleotide bases.

8. The nucleic acid of claim 1, wherein M$_0$ comprises between 5 and 10 bases.

9. A method for causing specific cleavage of a bond between two nucleotides in an RNA-containing molecule in vitro having the structure:

5'-XnUHZCUGANGAGYm-3' (see SEQ ID No. 1)

wherein each X and Y is independently any nucleotide base; n and m are independently between 5 and 40; H is C, U, or A; Z is a hairpin loop, comprising between 6 and 60 bases, and each U, C, G and A is a uracil, cytosine, guanosine, or adenosine-containing ribonucleotide, respectively, and N is any ribonucleotide; comprising the steps of contacting the RNA-containing molecule with nucleic acid having the structure:

3'-X'nMoY'm-5' wherein each X' and Y' are complementary nucleotide bases to each corresponding X and Y, and M$_0$ is a series of nucleotide bases active to cause the cleavage, under bond-cleaving conditions: and wherein M$_0$ contains no ribonucleotides.

10. The method of claim 9, wherein M$_0$ is 3'-aaagc-5', wherein a, g and c are adenosine, guanosine and cytosine-containing deoxyribonucleotides, respectively.

11. The method of claim 9, wherein said RNA-containing molecule has the structure chosen from:

5'-XnUCACCAGGAAACUGGUCUGANGAGYm-3' (see SEQ. ID NO. 2)

and

5'-XnUCUCCAGGAAACUGGACUGANGAGYm-3' (see SEQ. ID NO. 3).

12. The method of claim 11, wherein said nucleic acid has the structure:

3'-gcctcaaagcagtg-5' (see SEQ. ID NO. 4)

wherein, g, c, t and a are guanosine, cytosine, thymine and adenosine-containing deoxyribonucleotides.

13. The method of claim 9, wherein M$_0$ comprises between 5 and 10 bases.

14. The method of claim 9, wherein M$_0$ comprises all deoxyribonucleotide bases.

15. The method of claim 9, wherein X', M$_0$ and Y' comprise all deoxyribonucleotide bases.

* * * * *

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base. "N"in positions 6 to 40 may be present or absent.
"N"in positions 44 to 102 may
be present or absent. "N"in
positions 116 to 150 may be
present or absent.

( x i ) SEQUENCE DESCRIPTION: SEQ ID NO: 1:

NNNNNNNNN NNNNNNNNN NNNNNNNNN NNNNNNNNN UHNNNNNNN 50

NNNNNNNNN NNNNNNNNN NNNNNNNNN NNNNNNNNN NNNNNNNNN 100

NNCUGANGAG NNNNNNNNN NNNNNNNNN NNNNNNNNN NNNNNNNNN 150

( 2 ) INFORMATION FOR SEQ ID NO: 2:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
        base. "N"in positions 6 to
        40 may be present or absent.
        " N"in positions 70 to 104 may
        be present or absent.

( x i ) SEQUENCE DESCRIPTION: SEQ ID NO: 2:

NNNNNNNNN NNNNNNNNN NNNNNNNNN NNNNNNNNN UCACCAGGAA 50

ACUGGUCUGA NGAGNNNNN NNNNNNNNN NNNNNNNNN NNNNNNNNN 100

NNNN 104

( 2 ) INFORMATION FOR SEQ ID NO: 3:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
        base. "N"in positions 6 to
        40 may be present or absent.
        " N"in positions 70 to 104 may
        be present or absent.

( x i ) SEQUENCE DESCRIPTION: SEQ ID NO: 3:

NNNNNNNNN NNNNNNNNN NNNNNNNNN NNNNNNNNN UCUCCAGGAA 50

ACUGGACUGA NGAGNNNNN NNNNNNNNN NNNNNNNNN NNNNNNNNN 100

NNNN 104

( 2 ) INFORMATION FOR SEQ ID NO: 4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GCCTCAAAGC AGTG 14

( 2 ) INFORMATION FOR SEQ ID NO: 5:

( i ) SEQUENCE CHARACTERISTICS:
        ( A ) LENGTH: 33 base pairs (B) TYPE: nucleic acid
        (C) STRANDEDNESS: single
        (D) TOPOLOGY: linear (xi) SEQUENCE DESCRIPTION: SEQ ID NO: 5:

CGGAGUCACC AGGAAACUGG UCUGAUGAGU CAC                   33

(2) INFORMATION FOR SEQ ID NO: 6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 6:

GTGACGAAAC TCCG                                         14

(2) INFORMATION FOR SEQ ID NO: 7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 7:

GTGACGAAAC TCCG                                         14

(2) INFORMATION FOR SEQ ID NO: 8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 8:

CGGAGUCACC AGGAAACUGG UCUGAUGAGU CAC                   33

(2) INFORMATION FOR SEQ ID NO: 9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 9:

GTGACGAAAC TCCG                                         14

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 10:

CGGAGUCUCC AGGAAACUGG ACUGAUGAGU CAC                   33

(2) INFORMATION FOR SEQ ID NO: 11:

(i) SEQUENCE CHARACTERISTICS:
        (A) LENGTH: 14 base pairs
        (B) TYPE: nucleic acid
        (C) STRANDEDNESS: single ( D ) TOPOLOGY: linear ( x i ) SEQUENCE DESCRIPTION: SEQ ID NO: 11:

GTGACGAAAC TCCG                                                                                        14

( 2 ) INFORMATION FOR SEQ ID NO: 12:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
            base.

( x i ) SEQUENCE DESCRIPTION: SEQ ID NO: 12:

NNNNNGUCNN NNNN                                                                                        14

( 2 ) INFORMATION FOR SEQ ID NO: 13:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
            base.

( x i ) SEQUENCE DESCRIPTION: SEQ ID NO: 13:

NNNNNNAGAA NNNNACCAGA GAAACACACG UUGUGGUAUA UUACCUGGUA                                                  50

( 2 ) INFORMATION FOR SEQ ID NO: 14:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

UGGCCGGCAU GGUCCCAGCC UCCUCGCUGG CGCCGGCUGG GCAACAUUCC                                                  50

GAGGGGACCG UCCCCUCGGU AAUGGCGAAU GGGAC                                                                  85

( 2 ) INFORMATION FOR SEQ ID NO: 15:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
            base.

( x i ) SEQUENCE DESCRIPTION: SEQ ID NO: 15:

NNNNNNUCN NNNNNNNNN NCUGANGAGN NNNNN                                                   36

( 2 ) INFORMATION FOR SEQ ID NO: 16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear (ix) FEATURE:
    (D) OTHER INFORMATION: The letter "N" stands for any base.

(xi) SEQUENCE DESCRIPTION: SEQ ID NO: 16:

NNNNNNNAAA GCNNNNNN                                                                  19